(12) United States Patent
Ahrens

(10) Patent No.: US 8,834,720 B2
(45) Date of Patent: Sep. 16, 2014

(54) APPARATUS FOR THE EXTRACORPOREAL TREATMENT OF BLOOD

(75) Inventor: Joern Ahrens, Baunatal (DE)

(73) Assignee: B. Braun Avitum AG, Melsungen (DE)

( * ) Notice: Subject to any disclaimer, the term of this patent is extended or adjusted under 35 U.S.C. 154(b) by 412 days.

(21) Appl. No.: 13/148,371

(22) PCT Filed: Feb. 5, 2010

(86) PCT No.: PCT/EP2010/000737
§ 371 (c)(1),
(2), (4) Date: Aug. 8, 2011

(87) PCT Pub. No.: WO2010/091826
PCT Pub. Date: Aug. 19, 2010

(65) Prior Publication Data
US 2011/0309019 A1     Dec. 22, 2011

(30) Foreign Application Priority Data
Feb. 11, 2009 (EP) ................................. 09001890

(51) Int. Cl.
| | | |
|---|---|---|
| *B01D 61/30* | (2006.01) | |
| *B01D 61/32* | (2006.01) | |
| *G01J 3/02* | (2006.01) | |
| *A61M 1/16* | (2006.01) | |
| *G01N 21/27* | (2006.01) | |
| *G01J 3/42* | (2006.01) | |

(52) U.S. Cl.
CPC ......... *A61M 1/16* (2013.01); *A61M 2205/3313* (2013.01); *G01N 21/278* (2013.01); *G01J 3/42* (2013.01); *G01J 3/0286* (2013.01); *G01J 3/02* (2013.01); *G01J 3/027* (2013.01); *G01N 21/274* (2013.01); *A61K 1/1609* (2014.02)
USPC ......... 210/645; 210/94; 210/96.2; 210/321.6; 210/742; 210/745; 356/39; 356/436; 600/368; 600/407; 604/6.09; 604/65

(58) Field of Classification Search
CPC ...... B01D 61/243; B01D 61/30; B01D 61/32; A61M 1/16; A61M 1/1692; A61M 2001/1617; A61M 2001/1619; A61M 2005/3306; A61M 2205/3313; A61M 1/1607; A61M 1/1609; A61M 1/1617; A61M 1/1619; A61M 1/1605; G01J 3/0205; G01J 3/0208; G01J 3/021; G01J 3/02; G01J 3/027; G01J 3/026; G01J 3/42; G01J 21/274; G01J 21/278
USPC ............... 210/94, 96.2, 321.6, 645, 646, 739, 210/745, 149, 742; 604/5.01, 6.01, 6.09, 604/65; 356/39, 436, 440; 250/238, 505.1, 250/573–576; 600/368, 401, 407
See application file for complete search history.

(56) References Cited

U.S. PATENT DOCUMENTS

| | | |
|---|---|---|
| 4,281,245 A | 7/1981 | Brogardh et al. |
| 4,433,238 A | 2/1984 | Adolfsson et al. |

(Continued)

FOREIGN PATENT DOCUMENTS

| | | |
|---|---|---|
| DE | 102005063263 | 7/2007 |
| EP | 1083948 A1 | 3/2001 |

(Continued)

OTHER PUBLICATIONS

Fridolin et al., "On-line monitoring of solutes in dialysate using absorption of ultraviolet radiation: Technique descriptions," The Intl. Journal of Artificial Organs, vol. 25, No. 8, 2002, pp. 748-761.

(Continued)

*Primary Examiner* — Joseph Drodge
(74) *Attorney, Agent, or Firm* — RatnerPrestia

(57) ABSTRACT

Apparatus and methods for the extracorporeal treatment of blood are described. The apparatus includes a dialyzer which is separated into a first and second chamber by a semipermeable membrane, wherein the first chamber is disposed in a dialysis fluid path and the second chamber can be connected to the blood circulation of a patient by way of a blood inflow conduit and a blood outflow conduit, a feed for fresh dialysis fluid, a discharge for spent dialysis fluid, a measuring device disposed within the discharge for determining the absorption of the spent dialysis fluid flowing through the discharge, wherein the measuring device has at least one radiation source for substantially monochromatic electromagnetic radiation, and a detector system for detecting the intensity of the electromagnetic radiation, wherein means are provided to compensate for changes that occur in the intensity of the electromagnetic radiation of the radiation source and/or the sensitivity of the detector system.

16 Claims, 2 Drawing Sheets

(56) References Cited

U.S. PATENT DOCUMENTS

| | | | |
|---|---|---|---|
| 5,457,535 A * | 10/1995 | Schmidtke et al. | 356/364 |
| 5,670,050 A * | 9/1997 | Brose et al. | 210/646 |
| 5,680,410 A * | 10/1997 | Kim et al. | 372/34 |
| 5,825,399 A | 10/1998 | Orlicki et al. | |
| 6,027,256 A * | 2/2000 | Nightingale et al. | 385/92 |
| 6,527,728 B2 * | 3/2003 | Zhang | 600/500 |
| 6,666,840 B1 * | 12/2003 | Falkvall et al. | 604/5.04 |
| 7,002,670 B2 * | 2/2006 | Wariar et al. | 356/39 |
| 8,054,452 B2 * | 11/2011 | Bado et al. | 356/39 |
| 2003/0048432 A1 * | 3/2003 | Jeng et al. | 356/39 |
| 2003/0231294 A1 * | 12/2003 | Wariar et al. | 356/39 |
| 2006/0139577 A1 | 6/2006 | Ikeda et al. | |
| 2007/0023334 A1 * | 2/2007 | Hallstadius et al. | 210/94 |
| 2009/0032111 A1 | 2/2009 | Tong et al. | |
| 2010/0165324 A1 * | 7/2010 | Womble et al. | 356/39 |
| 2013/0020237 A1 * | 1/2013 | Wilt et al. | 210/85 |

FOREIGN PATENT DOCUMENTS

| | | |
|---|---|---|
| EP | 2005982 A1 | 12/2008 |
| WO | 9923479 | 5/1999 |
| WO | 9962574 | 12/1999 |
| WO | WO 2004/003290 | 1/2004 |
| WO | WO 2007/077208 | 7/2007 |

OTHER PUBLICATIONS

International Search Report, mailed May 27, 2010.

* cited by examiner

APPARATUS FOR THE EXTRACORPOREAL TREATMENT OF BLOOD

CROSS REFERENCE TO RELATED APPLICATIONS

This application is the U.S. national phase application of PCT International Application No. PCT/EP2010/000737, filed Feb. 5, 2010, which claims priority to European Patent Application No. EP 09001890.4, filed Feb. 11, 2009, the contents of such applications being incorporated herein by reference.

BACKGROUND OF THE INVENTION

In patients with reduced or no renal function at all, waste products including toxic substances are removed by a kidney replacement therapy, wherein the blood of the patient is fed from the patient to the artificial kidney, respectively the dialyzer, by a blood supply conduit. Inside the artificial kidney, respectively the dialyzer, the blood of the patient is brought into contact with the dialysis fluid via a semi-permeable membrane. The dialysis fluid contains different salts in such a concentration that the waste products including the toxic substances are transferred from the blood of the patient into the dialysis fluid by diffusion and convection. The blood such cleaned from the waste products is fed back into the blood circulation of the patient via a blood outflow conduit connected to the dialyzer.

For quantification of the result of the kidney replacement therapy, it is necessary to control the efficiency of the kidney replacement therapy directly or online. Therefore, the so-called Kt/V model was developed. Therein, the Kt/V value is a parameter for estimation of the efficiency of a kidney replacement therapy, wherein the clearance K stands for the volume flow of the purified uremic substances, t for the time of treatment, and V for the volume of distribution of the patient. Thereby, K as well as V is related each to the particular waste product. Usually, the efficiency of a kidney replacement therapy is described using urea as a waste product, so that K describes the urea clearance and V the distribution volume of urea in the patient, which basically corresponds to the body water of the patient.

From EP1083948A1 and EP2005982A1, it is known to estimate the Kt/V value and the reduction rate RR, respectively, spectrophotometrically for a particular waste product during the kidney replacement therapy with the help of a measuring device located in the outflow Kt/V value using UV radiation and its absorption by substances obligatory excreted by urine in the dialysis fluid.

These known apparatus have been shown, however, that a consistent intensity of the radiation of the radiation source and a consistent sensitivity of the detector system could not be guaranteed neither over the operating time of the radiation source nor during a single kidney replacement therapy. Consequently, the absorption measurement in the used dialysis fluid during different treatments and also during a single treatment time is based on variable radiation intensities of the radiation source and/or a modified output signal for a constant input signal of the detection system. This implicates that the Kt/V value based on the absorption measurement and the reduction rate RR based on the absorption measurement, respectively, of a particular product are not corresponding to the real values. On the contrary, the absorption measurement in the spent dialysis fluid and, thus, the statement concerning the Kt/V value and the reduction rate RR, respectively, is falsified for a particular waste product.

Therefore, it is the problem to develop an apparatus according to the generic term of claim 1 in such a way that a reliable and genuine statement about the Kt/V value and the reduction rate RR, respectively, of a kidney replacement therapy is obtained by the absorption measurement.

A further problem is to provide a method for obtaining a reliable and genuine statement about the Kt/V value and the reduction rate RR, respectively, of a kidney replacement therapy.

SUMMARY OF THE INVENTION

The problem related to an apparatus is solved by an apparatus with the features of claim 1. Advantageous forms are subject matter of dependent claims 2-14.

A reliable and genuine statement about the Kt/V value and the reduction rate RR, respectively, of a kidney replacement therapy will be obtained by the invention, wherein means are provided to compensate for an aging of the measurement apparatus during the operating time and occurring changes of the intensity of the electromagnetic radiation of the radiation source and/or the sensitivity of the detection systems during the treatment time.

It has been shown that the decreasing intensity of the radiation source over its operational time is caused primarily by an aging process of the radiation source. Since the working intensity $I_0$ of the radiation source in such an apparatus is normally smaller than the maximum intensity $I_{max}$ of the radiation source, a decrease of the radiation intensity due to the operating time can simply be compensated for by tracking of the radiation intensity of the radiation source. Thus, the radiation intensity is measured after absorption of fresh dialysis fluid by the detector system at the beginning of each treatment. As soon as deviations of this radiation intensity from the radiation intensity of the pre-defined nominal occur, this deviation is compensated. By this measure, the absorption measurements of the inventive apparatus are normable over the whole operating time, because they are always based on the same radiation intensity after absorption of fresh dialysis fluid.

Furthermore, it has been shown, too, that during a kidney replacement therapy a constant reference signal of the radiation intensity, which is generated by detection of the radiation intensity without absorption, also cannot be guaranteed. It has been shown that this is due to temperature fluctuations of the radiation source as well as of the detection source. It has been shown to be advantageous, therefore, that a temperature control is provided as means for compensation, by which the temperature of the radiation source is adjustable to a pre-defined working temperature range $\Delta T_1$ and/or the temperature of the detection system is adjustable to a pre-defined working temperature $\Delta T_2$. The signaling intensity of the radiation source as well as the sensitivity of the detection system have shown a clear stabilization by this measure, wherein the stability and subsequently the significance of the finally obtained results of the Kt/V values and reduction rate RR can be significantly increased once again by the combination of the two alternative measures.

Just the compensation of the intensity change of the electromagnetic radiation of the radiation source or of the sensitivity of the detection system is already leading to clearly improved statements about the Kt/V value and the reduction rate RR, respectively, for a particular waste product. A further significant improvement of these statements can be reached if both measures—a compensation of the change of the intensity of the electromagnetic radiation of the radiation source on the one hand and a compensation of the change of the sensitivity of the detection system on the other hand—are integrated into the inventive apparatus.

It has further been shown to be advantageous that an electronic control is provided as a means for compensation of the aging process of the radiation source, with the help of which the intensity I of the electromagnetic radiation of the radiation source is adjustable in such a way that intensities $I_{44}$ pre-defined at the detection system are detectable after absorption by fresh dialysis fluid and/or $I_{45}$ pre-defined at the detection system are detectable without absorption by fresh dialysis fluid.

Thereby, it has been shown to be advantageous that the electronic control is built as a control circuit, because such control circuits are already technically sophisticated and easy to use.

Because the absorption of substances obligatory excreted by urine is very good in the UV-range and essentially at 280 nm, it is appropriate to use a light emitting diode (LED) as a radiation source, which in its working temperature range $\Delta T_1$ emits essentially electromagnetic radiation of the wave length 280 nm.

It is further advantageous if the detection system consists of at least one photo detector and preferably of two photo detectors. For estimating the absorption of the dialysis fluid always on the same basis using one photo detector only, it has to be anticipated, however, that the signaling intensity of the radiation emitted by the radiation source is not constant over time. Therefore, it is clearly better to use two detectors, wherein one measures the intensity of the radiation source and one measures the intensity of the radiation after passage through the spent dialysis fluid.

A particularly effective embodiment of the invention consists in the fact that in the optical path of the electromagnetic radiation between the radiation source and the outflow for spent dialysis fluid a partially transmissive mirror or an optical device is arranged for beam division or beam deflection, so that a part of the electromagnetic radiation by the spent dialysis fluid is fed to the first photo detector and the rest is fed to the second detector.

According to a further embodiment of the invention the control variable of the control circuit is the intensity of the electromagnetic radiation at the first detector and the regulating variable is the electric current of the radiation source, wherein the measured intensity at the second detector is savable as reference value for the entire kidney replacement therapy. By this measure, a particularly good control of the radiation intensity of the electromagnetic source is guaranteed during the whole operating time of the radiation source.

In this context, it has been shown to be particularly advantageous if during the particular kidney replacement therapy the reference value of the intensity measured at the second detector is the control variable of a second control circuit and the electric current of the radiation source is the regulating variable of this second control circuit. Thereby, a change of the reference value can be basically compensated for without delay during a kidney replacement therapy.

For designing the temperature control as simple and effectively as possible, it has been shown to be advantageous if the temperature control has a cooling body for the LED and/or the detector system and the detectors, respectively.

Alternatively or additionally it is also possible that the temperature regulation has a water-cooling for the LED and/or the detectors, respectively.

Further, alternatively or additionally the temperature control can have one or more fans for the LED and/or the detectors.

It has been shown to be particularly advantageous if the temperature control has alternatively or additionally one or more electrothermal transducers, for instance Peltier elements for temperature control of the LED and/or the detectors.

The problem related to the method is solved by a method with all features of claim 15.

Further goals, advantages, features and possible applications of the present invention are evident from the following description of the embodiment examples with the figures. Therein, all described and/or illustrated features, alone or in reasonable combination, form the subject matter of the present invention, also independently of their summary in the claims and their references.

DESCRIPTION OF THE DRAWINGS

It is shown in.

DETAILED DESCRIPTION OF THE INVENTION

Figure 1:
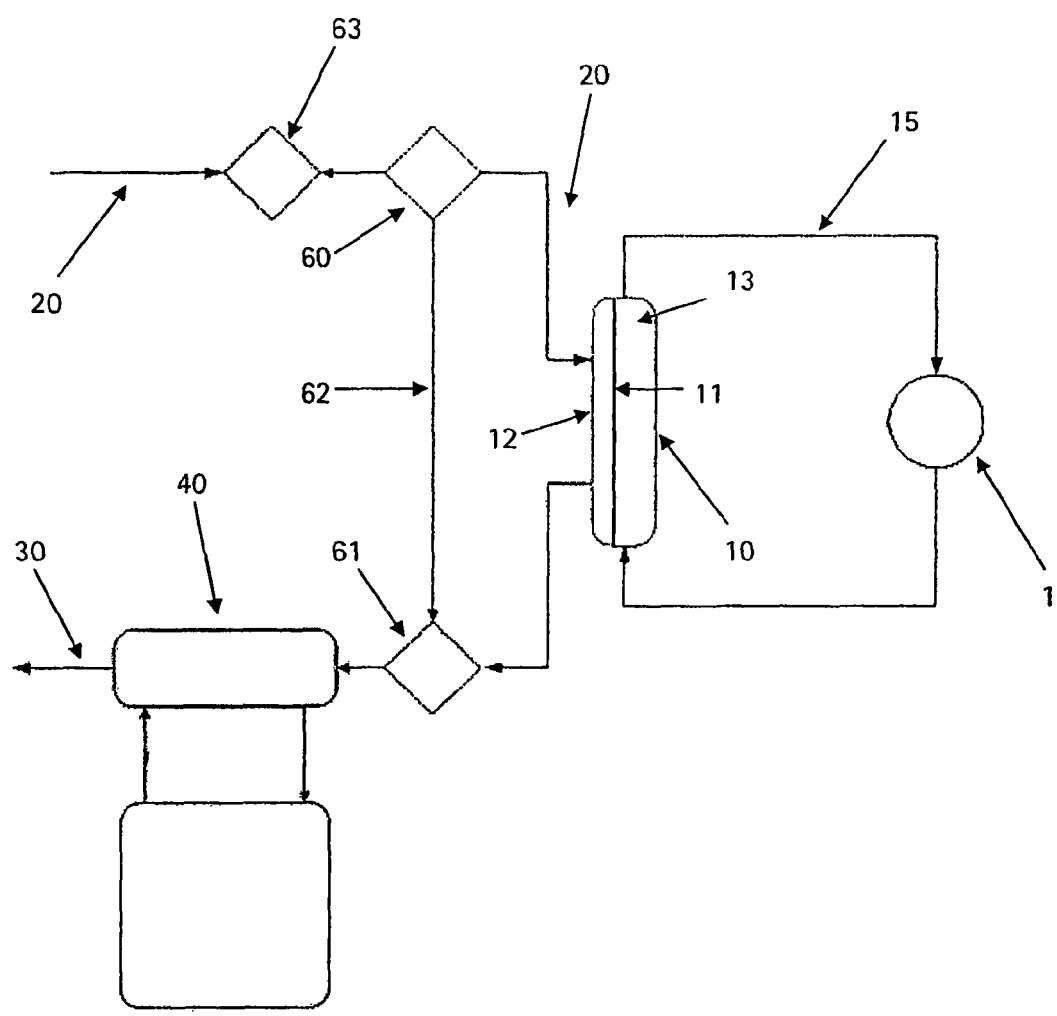
FIG. 1: a schematic representation of an embodiment example of an inventive apparatus.

In FIG. 1, an embodiment example of an inventive apparatus is presented in a condition connected to patient 1. Thereby, patient 1 is connected to a dialyzer 10 by a blood inflow conduit 14. A blood outflow conduit 15 feds the purified blood to the blood circulation of the patient.

The dialyzer 10 is separated into first and second chambers 12, 13 by a semipermeable membrane 11, wherein the blood of patient 1 to be purified is fed through first chamber 13, and dialysis fluid, which is able to take up waste products and toxic substances contained in the blood of patient 1, is fed through the second chamber 12. The transport of the waste products and toxic substances from the blood of patient 1 into the dialysis fluid happens by diffusion and convection via the semipermeable membrane 11. The dialysis fluid is supplied to the second chamber 12 of the dialyzer 10 via a feed 20. Therein, a pump is provided in feed 20 for supply of the dialysis fluid as well as a valve 60, which serves for leading the dialysis fluid around instead of into the dialyzer 10 via a bypass into a discharge 20 for the dialysis fluid. In the discharge 30, there is also a valve 61, which is connected to valve 60 in feed 20 via bypass 62.

After waste products and toxic substances have been transferred from the blood of the patient 1 into the dialysis fluid in dialyzer 10, the spent dialysis fluid is disposed over the discharge 30. A measuring device 40 is disposed within the discharge 30, which can be used for estimation of the absorption of the spent dialysis fluid using a radiation source 41 for electromagnetic radiation, particularly with a LED 43 working in the UV range, and a detector system 42, which in the present embodiment example according to FIG. 2 consists of a partially transmissive mirror 46 and two photo detectors 44 and 45.

Figure 2:
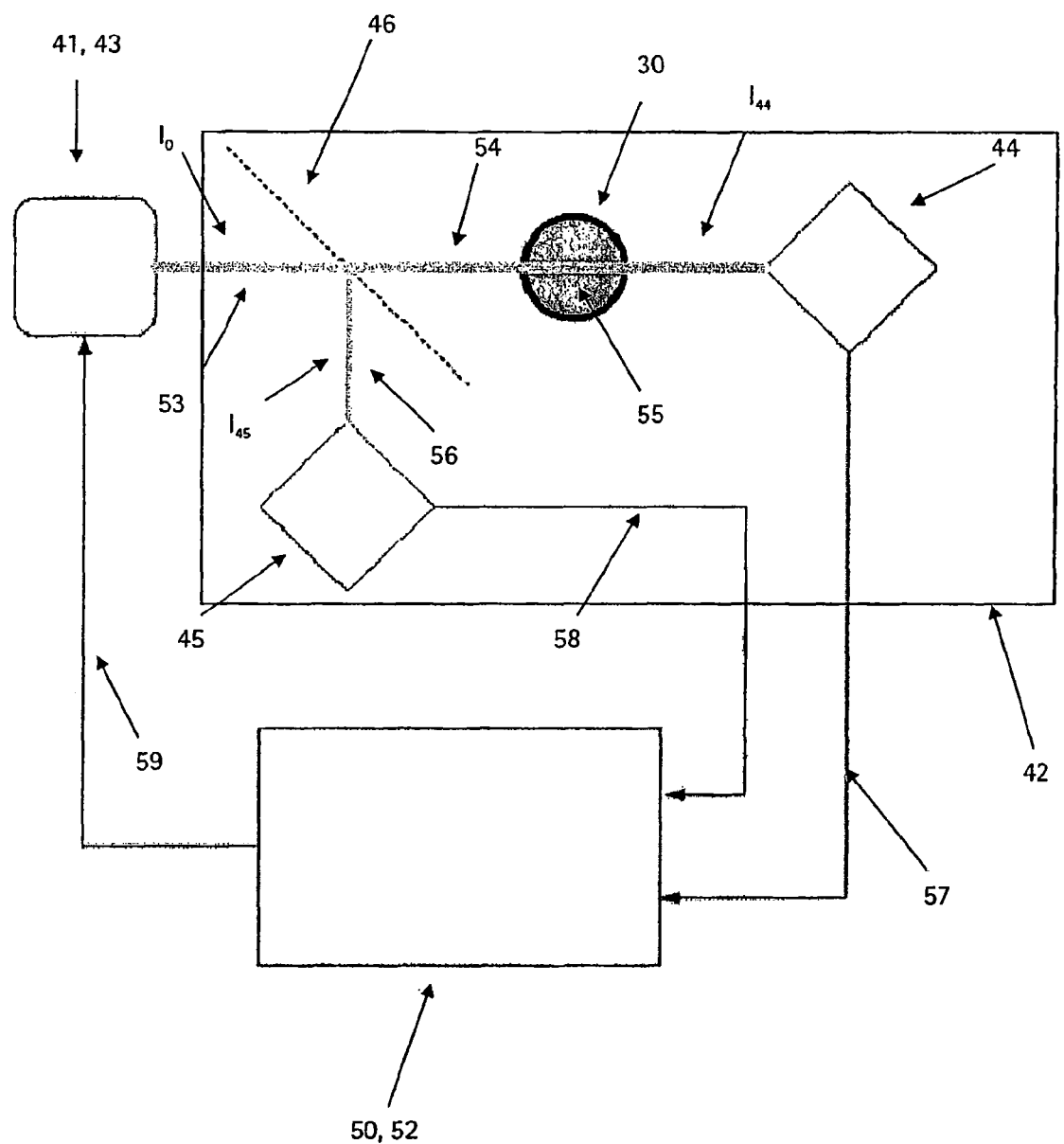
FIG. 2: a schematic representation of an embodiment example of a measuring apparatus or a detection system, respectively, of an inventive apparatus.

The mode of operation of the measuring device 40 and the detector system 42 is the following: According to the principle of two-beam-spectroscopy as shown in FIG. 2, the LED 43 is emitting UV-light of a wavelength of about 280 nm as radiation 53, which is divided by the partially transmissive mirror 46. A part 54 of the radiation 53 passes through the partially transmissive mirror 46, and the remaining part 56 of the radiation 53 is reflected by the partially transmissive mirror 46 onto the detector 45. A certain part of the electromagnetic radiation of part 54 is absorbed by substances obligatory excreted by urine contained in the spent dialysis fluid 55. The part of part 54, which has not been absorbed by substances obligatory excreted by urine, is recorded by detector 44. The part 56 of the electromagnetic radiation recorded by detector 45 is consequently independent of substances obligatory excreted by urine in the dialysis fluid 55 and over the partially transmissive mirror directly proportional to the intensity I of the radiation source.

Since substances obligatory excreted by urine, which have been removed from the blood in the dialyzer are contained in the dialysis fluid 55 in discharge 30 and these substances obligatory excreted by urine can absorb electromagnetic radiation of the wavelength 280 nm, the absorption of substances obligatory excreted by urine in discharge 30 can be estimated using the intensity measured at detector 44. Thereby, the change of absorption by substances obligatory excreted by urine, which serves as a basis for the estimation of the Kt/V value, can be measured during the treatment.

With increasing concentrations of substances obligatory excreted by urine in the dialysis fluid 55 the signal at detector 44 is decreased because of the rising absorption. The change of absorption serves for estimation of an e-function, from which the Kt/V value is calculated.

For obtaining exact information about the absorption during the treatment time fluctuations of the intensity I of the LED 43 have to be avoided. Usually, a compensation of fluctuations of a light source in a two-beam-spectroscopy as in the present case is done by following formula (in relation to absorption A), wherein the intensities $I_{44}$ and $I_{45}$ at the detectors 44 and 45, respectively, are converted in corresponding signals:

$$A(t) = \log\left(\frac{U_{44}}{U_{45}} \cdot \frac{U_{45\_t}}{U_{44\_t}}\right)$$

With
$U_{44}$=signal at detector 44 with fresh dialysis fluid
$U_{45}$=signal at detector 45 at the beginning
$U_{44\_t}$=signal at detector 44 at time point t during the therapy
$U_{45\_t}$=signal at detector 45 at time point t during the therapy With the apparatus according to FIGS. 1 and 2 the intensity $I_0$ is kept at a constant level during the therapy, so that $U_{45}=U_{45\_t}\sim I_0$, wherein $I_0$ is arbitrary in the operating range of the LED. Thereby, the formula for absorption A is reduced to $$A(t) = \log\left(\frac{U_{44}}{U_{44\_t}}\right)$$

The absorption results in a curve, which can be described by an e-function, from which Kt/V=b*t can be estimated by A(t)=a*exp(b*t).

For compensation of the measurement errors occurring in apparatuses known in the art, particularly by aging and temperature instability, two approaches exist:
Signaling stability by electronic control of the emitted electromagnetic radiation on a pre-defined level
Temperature stability by temperature control The problem of aging can occur particularly at radiation source 41 or LED 43, respectively, discharge 30 as well as detector system 42 or the two detectors 44 and 45, respectively, and can cause a change of the properties.

With the use of the electronic control it is possible to compensate for changes by aging and temperature fluctuations very precisely. The electromagnetic radiation of LED 43 loses intensity by aging at a constant current during the operation time, and at rising temperature it reacts also with a decreasing electromagnetic radiation. Also there is an aging at the detectors 44 and 45. By aging the partially transmissive mirror affects the transmissibility as well as the relation of the optical path between $I_0$ and $I_{44}$ and $I_{45}$. There can also occur a constant haze in discharge 30.

By a pre-defined nominal value $I_{44\_soll}$ of the intensity of the electromagnetic radiation at detector 44, wherein the electromagnetic radiation has passed through a clear dialysis fluid without substances obligatory excreted by urine in discharge 30, the measuring range or the resolution of the detector system 42 or the detector 44, respectively, are used optimally. Thereby, changes in the system by aging are recognized and compensated for, whereby this results also in a test of the performance of the measuring system. Thereby, it is guaranteed that the quality of the signal, the measuring range, the measuring resolution and the reproducibility are constant during the entire life time.

The formula for the absorption with the nominal value $I_{44\_soll}$ results in:

$$A(t) = \log\left(\frac{U_{44\_Soll}}{U_{44\_t}}\right)$$

The electronic control is performed in two steps:

At the beginning of the kidney replacement therapy, prior to connection of the patient or in the bypass, respectively, pure dialysis fluid without substance obligatory excreted by urine is in discharge 30. In this operating mode at first a regulation of the electric current of the radiation source 41 is set as regulating variable, so that the pre-defined nominal value $I_{44\_soll}$ of the radiation intensity is detected as entry signal at detector 44. At reaching the pre-defined nominal value $I_{44\_soll}$ at detector 44 the intensity value $I_{45}$ is saved by detector 45 and serves as nominal value $I_{45\_soll}$ during a second regulation during the following kidney replacement therapy. Thus, now an adjustment of the electric current of the radiation source 41 or the LED, respectively, occurs as a regulating variable for the intensity value $I_{45\_soll}$ at detector 45.

The adjustment is conducted with an adaptive regulator, which at first detects in an automated fashion the transfer function of the system $F_{44}(43,44,46,30)=U_{44}$, which depends on the LED 43, the detector 44, the partially transmissive mirror 46 as well as the discharge 30, and the transfer function of the system $F_{45}(43,46,45)=U_{45}$, which depends on the LED 43, the detector 45 and the partially transmissive mirror 46. This adjustment can also be carried out with any other kind of regulation, which would, however, result in a slower transient condition.

The first control process at the beginning of the therapy occurs prior to the connection of the patient 1 or in the bypass 62, respectively, at which based on the appropriate setting of the valves 60 and 61 the fresh dialysis fluid is fed around the dialyzer 10, with fresh dialysis fluid without uremic substances. Using adaptive control and the transfer function $F_{44}$ the control process to the pre-defined nominal value of the radiation intensity $I_{44\_soll}\sim U_{44\_soll}$ is carried out at detector 44. Thereby the compensation of the aging happens by changing the electric current of the LED 43. If necessary amplifying factors of the electronic detector circuits can be adapted at the detectors 44 and 45, signal quality permitting. The resulting measured value at detector 45 is saved as nominal value $U_{45}$ for the second control process and serves as nominal value during the therapy to compensate for temperature fluctuations. Thereby the absorption is A=0, because $U_{44}=U_{44_t}$.

After connection of the patient 1 the detection of measured value of $U_{44_t}$ is done at detector 44. Substances obligatory excreted by urine change the measured value at detector 44 and the absorption results from:

$$A(t) = \log\left(\frac{U_{44}}{U_{44\_t}}\right)$$

Apart from the compensation of temperature fluctuations this approach facilitates also a constant measured value as well as a constant quality of the signal.

During a therapy, i.e. during a single kidney replacement therapy, an aging of the detectors 44 and 45 can be neglected. The system is controlled during the kidney replacement therapy to the nominal value $U_{45}$ at the detector 45, which facilitates a stable and constant emitted electromagnetic radiation independently of the flow of the dialysis fluid. Thus the temperature drift of the LED 43 or the intensity $I_0$, respectively, can be compensated for. The regulating variable of the control is the electric current of the LED 43, which is proportional to the intensity $I_0$ of the radiation emitted by LED 43. An absolute control to the detector 44 by a pre-defined value at the beginning, however, is not practical, because influences during the therapy cannot be compensated for.

The specification of a pre-defined nominal value in the first control process serves for definition of the measuring range of the electronics and at the same time defines the measuring resolution of the absorption of the measuring signal.

Amplifier circuits within the electronic control 52 not shown in the figures convert the signal of the detectors 44 and 45 into a measuring voltage, for which analog-digital-converters with a microprocessor-measuring value detector are available. This adaption of the amplifier circuits, which can be done prior to each single kidney replacement treatment only, may be done automatically prior to the kidney replacement therapy in parallel to the control of the current of the LED 43. During the treatment, however, only a control of the current is possible.

Using the temperature control the LED 43 and the detectors 44 and 45 reach an optimal operating temperature. At high temperatures the current as a regulating variable of the LED 43 has to be increased for keeping the emitted electromagnetic radiation at rising temperatures at a constant intensity. Vice versa at decreasing temperatures the current as regulating variable has to be decreased. An increase of the current is however only possible in the operating range of the LED 43 and accelerates the aging process. From experience tremendous temperature fluctuations occur in a dialyzer. Therefore it is practical to compensate for temperature fluctuations by a temperature control 51, so that the apparatus can be operated in optimal temperature range. The aging process is slowed down by such measures, too.

It is the goal of the temperature control to operate the LED 43 and the detectors 44 and 45 in the optimal temperature range and reach the optimal temperature range for these components quickly, respectively, so that during the therapy a change of the temperature can be reduced to a minimum. After disinfection higher temperatures can occur at the measuring device 40 or the LED 43, respectively, and/or the detector system 42 or the detectors 44 and 45, respectively, by heating of the system. Furthermore, by switching on the apparatus in the cold condition the self-generated heating of the system causes a cooling, which leads to very low temperatures at the beginning. Therefore it is necessary to bring the temperature into the operating range of the components as soon as possible, while the apparatus is prepared for the kidney replacement therapy, so that the electronic control 52 described above is in the nominal range of the temperature already at the beginning of the therapy or during the identification of the system, respectively. Thus it is possible to reduce even very small deviations of the detectors 44 and 45 related to a drift of a signal by temperature fluctuations to a minimum.

The temperature stabilization is carried out with a cooling body with water-cooling, which couples the flow temperature of the dialysis fluid directly with the cooling body of the LED 43 and/or the detectors 44 and 45. The heat capacity of the dialysis fluid is clearly higher than the one of the cooling body of the LED 43 and therefore defines the temperature, which is possible without additional technical effort. Thus it is possible to keep the temperature approximately constant in the operating range of the components and to bring the system into the optimal temperature range quickly.

It is however not possible without tremendous additional effort to keep the temperature stable enough so that it does not have further influence on the intensity of the radiation emitted by the LED 43. Consequently a stabilization of the light intensity $I_0$ has to be carried out in parallel with the electronic control 52 mentioned above.

A cooling can be carried out with other active and passive cooling methods, as well. As way of passive cooling, the LED 43 or the detectors 44 and 45, respectively, can be temperature-stabilized over the housing or a water-cooling. As an active cooling it is possible to use a fan which controls the temperature depending on the environmental temperature. It is also possible to control the temperature stabilization directly with a Peltier element or similar electrothermal converters.

The invention claimed is:
1. Apparatus for the extracorporeal treatment of blood with
   a dialyzer, which is separated into a first and second chamber by a semipermeable membrane, wherein the first chamber is disposed in a dialysis fluid pathway and the second chamber is connectable to the blood circulation of a patient by way of a blood inflow conduit and a blood outflow conduit,
   a feed for fresh dialysis fluid,
   a discharge for spent dialysis fluid,
   a measuring device disposed in the discharge for estimation of the absorption of the spent dialysis fluid flowing through the discharge, the measuring device comprising:
      at least one radiation source for substantially monochromatic electromagnetic radiation;
      a detector system for detecting the intensity of the electromagnetic radiation, the detector system comprising:
         a partially transmissive mirror configured to direct a first portion of the electromagnetic radiation to a first detector and to direct a second portion of the electromagnetic radiation to a second detector,
         wherein the first detector detects a first intensity of the first portion of the electromagnetic radiation after absorption of dialysis fluid; and
         the second detector detects a second intensity of the second portion of the electromagnetic radiation without absorption of dialysis fluid;

the measuring device configured to detect, with the first detector, an initial intensity of the first portion after absorption of fresh dialysis fluid prior to beginning an initial dialysis treatment as a first pre-defined intensity and configured to detect, with the first detector, a subsequent intensity of the first portion after absorption of fresh dialysis fluid prior to beginning a subsequent dialysis treatment; and an electronic control configured to adjust the electromagnetic radiation such that the detected subsequent intensity of the first portion after absorption of fresh dialysis fluid prior to the beginning of the subsequent dialysis treatment is adjusted to the first pre-defined intensity.

2. Apparatus according to claim 1, wherein a temperature control is provided as means for adjusting at least one of the temperature of the radiation source to a first pre-defined operating temperature or the temperature of the detector system to a second pre-defined operating temperature.

3. Apparatus according to claim 1, wherein the radiation source is formed as an LED.

4. Apparatus according to claim 3, wherein the LED essentially emits electromagnetic radiation of the wave length 280 nm.

5. Apparatus according to claim 3, wherein the first intensity of the electromagnetic radiation at the first detector is the control variable and the electric current of the radiation source is the regulating variable and the second intensity at the second detector is savable as a reference value.

6. Apparatus according to claim 5, wherein the reference value is the control variable of a second control circuit and the electric current of the radiation source is the regulating variable.

7. Apparatus according to claim 2, wherein the temperature control has a cooling body for the at least one of the LED, the detector system or the detectors, respectively.

8. Apparatus according to claim 2, wherein the temperature control has a water-cooling for at least one of the LED or the detectors.

9. Apparatus according to claim 2, wherein the temperature control has one or more fans for at least one of the LED or the detectors.

10. Apparatus according to claim 2, wherein the temperature control has one or more electrothermic converters for controlling the temperature of the LED and/or the detectors.

11. The apparatus of claim 1, the measuring device further configured to detect, with the second detector, a second pre-defined intensity as the second intensity of the second portion without absorption of dialysis fluid prior to beginning dialysis treatments and when the first intensity of the first portion is adjusted to the first pre-defined intensity; and the electronic control being further configured to adjust the electromagnetic radiation such that, during dialysis treatments, the second intensity of the second portion of the electromagnetic radiation is adjusted to the second pre-defined intensity.

12. The apparatus of claim 10, wherein the one or more electrothermic converters comprises Peltier elements.

13. A method for compensating for changes in intensity of an electromagnetic radiation source and/or detector system of an apparatus for extracorporeal treatment of blood, the method comprising the steps of:

emitting electromagnetic radiation from the electromagnetic radiation source to a partially transmissive mirror;

diverting, by the mirror, a first portion of the electromagnetic radiation through fresh dialysis fluid to a first detector for detecting an intensity of the first portion;

detecting, at the first detector and prior to the beginning of an initial dialysis treatment, an initial intensity of the first portion that is diverted through fresh dialysis fluid;

designating the detected initial intensity of the first portion as a first pre-defined intensity;

detecting, at the first detector and prior to the beginning of a subsequent dialysis treatment, a subsequent intensity of the first portion that is diverted through fresh dialysis fluid; and adjusting, by an electric control, the electromagnetic radiation source such that, prior to the beginning of the subsequent dialysis treatment, the subsequent intensity of the first portion diverted through fresh dialysis fluid is adjusted to the first pre-defined intensity.

14. The method of claim 13, further comprising the steps of:

diverting, by the mirror, a second portion of the electromagnetic radiation to a second detector without passing through dialysis fluid;

detecting, at the second detector and prior to the beginning of the initial dialysis treatment, an intensity of the second portion when the intensity of the first portion detected at the first detector is at the first pre-defined intensity;

designating the detected intensity of the second portion as a second pre-defined intensity; and controlling, by the electric control, the electromagnetic radiation source, such that, during dialysis treatments, the intensity detected of the second portion is controlled to the second pre-defined intensity.

15. The method of claim 13, further comprising the step of:

controlling, by a temperature control and during dialysis treatments, the temperature of the electromagnetic radiation source to a first pre-defined operating temperature.

16. The method of claim 13, further comprising the step of:

controlling, by a temperature control and during dialysis treatments, the temperature of the detector system to a second pre-defined operating temperature.

* * * * *

UNITED STATES PATENT AND TRADEMARK OFFICE
CERTIFICATE OF CORRECTION

| | | |
|---|---|---|
| PATENT NO. | : 8,834,720 B2 | Page 1 of 1 |
| APPLICATION NO. | : 13/148371 | |
| DATED | : September 16, 2014 | |
| INVENTOR(S) | : Joern Ahrens | |

It is certified that error appears in the above-identified patent and that said Letters Patent is hereby corrected as shown below:

On the Title Page, Item [30], Foreign Application Priority Data, "09001890" should read --09001890.4--

Signed and Sealed this
Twentieth Day of January, 2015

Michelle K. Lee
*Deputy Director of the United States Patent and Trademark Office*